US012765889B2

(12) United States Patent
Endres et al.

(10) Patent No.: US 12,765,889 B2
(45) Date of Patent: Oct. 20, 2026

(54) SET FOR THE ENDOSCOPIC FIXATION OF AN IMPLANT IN AN INTERVERTEBRAL DISK BY MEANS OF A NAIL OR PIN

(71) Applicant: BioTissue SA, Geneva (CH)

(72) Inventors: Michaela Endres, Geneva (CH); Jan-Philipp Kruger, Geneva (CH); Sebastian Schroder, Geneva (CH)

(73) Assignee: BioTissue SA, Geneva (CH)

( * ) Notice: Subject to any disclaimer, the term of this patent is extended or adjusted under 35 U.S.C. 154(b) by 0 days.

(21) Appl. No.: 19/210,649

(22) Filed: May 16, 2025

(65) Prior Publication Data

US 2025/0275778 A1 Sep. 4, 2025

Related U.S. Application Data

(62) Division of application No. 17/440,290, filed as application No. PCT/EP2020/000073 on Mar. 19, 2020, now Pat. No. 12,329,394.

(30) Foreign Application Priority Data

Mar. 19, 2019 (EP) .................................... 19163831

(51) Int. Cl.
*A61B 17/17* (2006.01)
*A61B 17/70* (2006.01)
*A61B 17/00* (2006.01)

(52) U.S. Cl.
CPC ...... *A61B 17/1757* (2013.01); *A61B 17/7074* (2013.01); *A61B 2017/00004* (2013.01)

(58) Field of Classification Search
CPC .................................................. A61B 17/1757
See application file for complete search history.

(56) References Cited

U.S. PATENT DOCUMENTS

2004/0092933 A1* 5/2004 Shaolian ............ A61B 17/1675 606/279
2005/0004593 A1* 1/2005 Simonson ............ A61B 17/025 606/191
2005/0216087 A1 9/2005 Zucherman et al.
2008/0033432 A1 2/2008 McGraw et al.
(Continued)

FOREIGN PATENT DOCUMENTS

DE 102010052113 A1 5/2012
WO WO-2012065753 A1 * 5/2012 ............ A61F 2/4611

OTHER PUBLICATIONS

International Preliminary Report on Patentability, WIPO, Sep. 16, 2021.

*Primary Examiner* — Christian A Sevilla
(74) *Attorney, Agent, or Firm* — Schwabe, Williamson & Wyatt, P.C.

(57) ABSTRACT

The invention relates to a set for the endoscopic fixation of an implant by means of a nail or pin. It comprises the following: an applicator sheath insertable through an endoscope into an intervertebral disk and through which an implant is insertable into an intervertebral disk defect; a drill wire guide sheath sized to be insertable into the applicator sheath; and a pusher for imparting blows during the fixation of an implant in the intervertebral disk by means of a nail or pin, wherein the pusher being sized to be insertable into the applicator sheath. In addition, the set may comprise an implant and or at least one nail or pin.

5 Claims, 5 Drawing Sheets

(56) References Cited

U.S. PATENT DOCUMENTS

Figure 1:
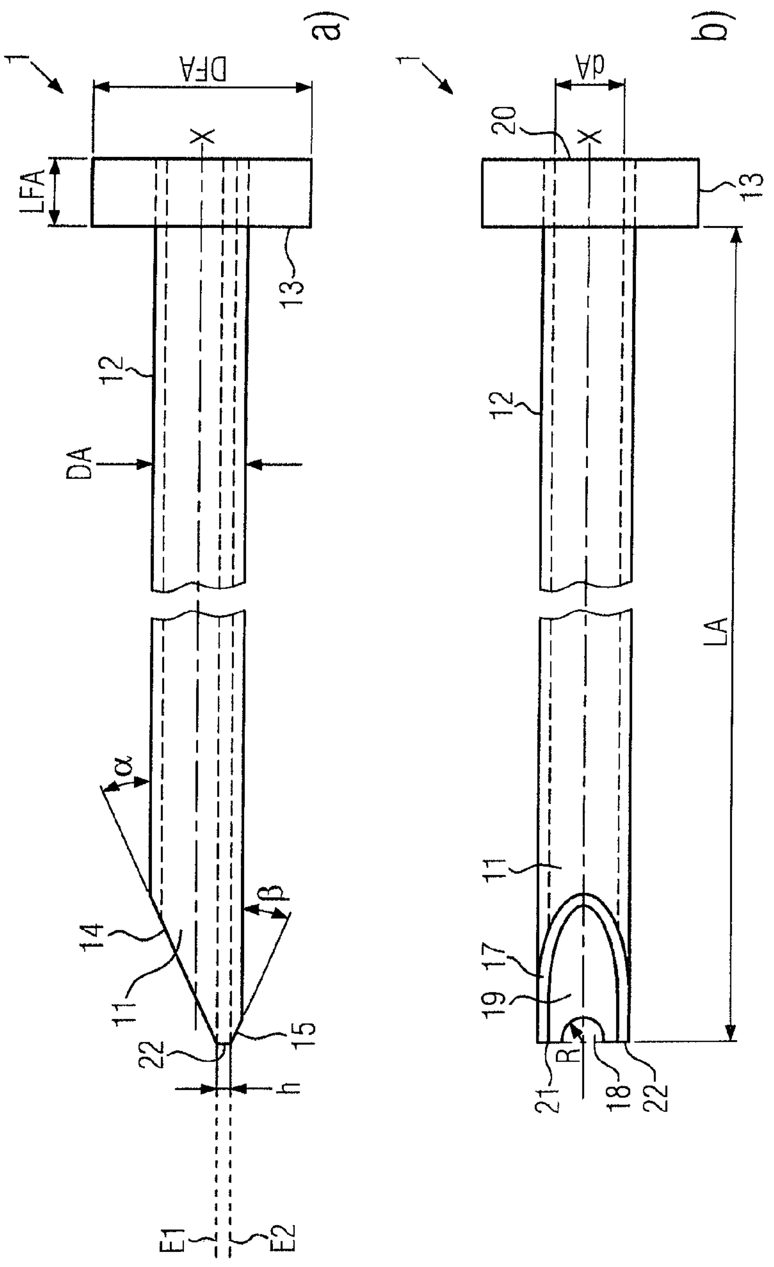

| | | | | |
|---|---|---|---|---|
| 2009/0143862 | A1* | 6/2009 | Trieu | A61B 17/70 606/301 |
| 2010/0016889 | A1 | 1/2010 | Ferree | |
| 2018/0228476 | A1 | 8/2018 | Cannon et al. | |

* cited by examiner

| Designation | Dimension |
| --- | --- |
| applicator sheath | LA = 215-290 mm |
| | Ø inner dA = 3.4 mm |
| | Ø outer DA = 4.0 mm |
| drill wire guide sheath | LB = 210-285 mm |
| | Ø inner dB = 2.4 mm |
| | Ø outer DB = 3.0 mm |
| pusher | LS = 220-305 mm |
| | Ø outer DS = 3.0 mm |

Fig. 4

| Designation | Dimension | Tolerance |
|---|---|---|
| **applicator sheath** | LA = 240 mm (without flange) | ± 1 mm |
| | angles α, β = 25° | ± 5° |
| | 2 tip ends/ teeth with h = 1 mm | ± 0.5 mm |
| | Ø inner dA = 3.4 mm | - 0 mm |
| | Ø outer DA = 4.0 mm | + 0.05 mm |
| | Ø flange DFA: 24 mm | - 1 mm/+ 6 mm |
| **drill wire guide sheath** | LB = 235 mm (without flange) | - 1 mm/+ 0 mm |
| | Ø inner dB = 2.4 mm | - 0 mm |
| | Ø outer DB = 3.0 mm | + 0.04 mm |
| | Ø outer flange DFB = 12 mm | - 1 mm/+ 6 mm |
| **pusher** | LS = 255 mm (without head) | ± 0.5 mm |
| | length mandrel LD = 2 mm | ± 0.1 mm |
| | Ø mandrel DD = 1.0 mm | - 0 mm |
| | Ø outer DS = 3.0 mm | + 0.04 mm |
| | length head LSK = 15 mm | ± 2 mm |
| | Ø head DSK = 10 mm | ± 2 mm |

Fig. 5

SET FOR THE ENDOSCOPIC FIXATION OF AN IMPLANT IN AN INTERVERTEBRAL DISK BY MEANS OF A NAIL OR PIN

CROSS REFERENCE TO RELATED APPLICATIONS

The present application is a division of U.S. patent application Ser. No. 17/440,290, filed on Sep. 17, 2021, which is a national phase entry under 35 USC 371 and claims priority benefit of PCT/EP2020/00073 having an (International) filing date of Mar. 19, 2020, which claims priority to European Patent Application No. 19163831.1, filed on Mar. 19, 2019, the disclosures of which are hereby incorporated by reference in their entirety.

FIELD OF THE INVENTION

The invention relates to a set for the endoscopic fixation of an implant in an intervertebral disk by means of a nail or pin.

PRIOR ART

In the vertebral column the intervertebral disks are arranged as shock absorbers between the single vertebrae and they have a buffer function by absorbing vibrations. They consist of a soft gelatinous core and an outer solid fiber ring which is necessary for the required stability. In the case of permanent incorrect or too strong load and age-related degeneration of the tissue, often, the result is a bulging disk. In such a case the gelatinous core (nucleus pulposus) presses the outer fiber ring against the posterior longitudinal ligament which shields the intervertebral disk from the spinal canal. Little by little, small initial cracks are formed in the outer fiber ring (annulus fibrosus). So, it is possible that a part of the viscous core of the intervertebral disk leaks from the ring and gets into the vertebral canal. When then this leaked gelatinous mass presses onto a nerve root, this results in massive pains, in sensibility disorders or paralyses. A surgical removal of the leaked gelatinous mass (sequestrectomy) results in the decompression of the nerve roots and in the relief of the symptoms. In 92% of the cases the treatment shows good results. However, postoperatively, after two years a worsening of the symptoms can be diagnosed. The loss of the tissue results in a progression of the degeneration and concomitantly therewith in a reduction of the height of the intervertebral disk. Thus, the sequestrectomy is the treatment of the symptoms (pain by sequestrum), but not a treatment of the cause (degeneration of the intervertebral disk).

For a very high number of patients with the diagnosis slipped disk the development of novel regenerative therapies for the treatment of mesenchymal tissue defects is becoming increasingly important. Especially in the field of the therapy of slipped disks, there is an increasing demand for regenerative therapies which stimulate and support the self-healing forces. The predominant portion of the therapy options, both innovative and also established since many years, aims to maintain the height of the intervertebral disk after an event of a slipped disk. In such a case implants for maintaining the height of the intervertebral disk and/or for building up repair tissue are placed into the intervertebral disk. Here, one major problem is the squeezing out (sequestering) of the implant in the case of a load, because the fiber ring is damaged and does not heal. In existing surgical techniques by conglutinating the fiber ring or also by using a closure device, implants should be hindered to be squeezed out from the intervertebral disk. For this purpose, systems such as the CE certified Barricaid© or also the so-called Inclose System (Anulex Technologies, Inc., Minnetonka, MN (not certified for the EU)) have been used. Nevertheless, the problem of squeezing out of the implant in the case of a load could not be solved satisfactorily so far.

DESCRIPTION OF THE INVENTION

Thus, it is the object of the present invention to provide an operation set by means of which an implant can be inserted into an intervertebral disk, is fixed and wherein a corresponding operation method leads to permanently good results.

This object is solved by the independent patent claim 1. Advantageous embodiments of the invention arise from the dependent patent claims.

The invention relates to a set for the endoscopic fixation of an implant in an intervertebral disk by means of a nail or pin which has been adjusted innovatively to the special requirements during a corresponding operation at an intervertebral disk. In the context of the invention, at first, it has been recognized that it should be possible to fix an implant in an intervertebral disk by nails or pins which in particularly are resorbable. Thus, the invention is based on the idea for a novel surgical method. But, then, this novel surgical method requires a surgical set which is especially tailored for it.

A fixation of implants by means of a resorbable nail or pin is already known from other fields of medicine. So, a pin fixation is used in orthopedy in the case of the refixation of fragment parts of the meniscus. In addition, it is used for the fixation of resorbable implants in the case of articular cartilage defects in the knee. But, the properties of articular cartilage in the knee are substantially different from cartilaginous tissue of the intervertebral disk so that here a direct transfer to operations of intervertebral disks is not possible. Furthermore, existing instruments for the fixation of a pin in a knee joint are not suitable for conducting an operation at an intervertebral disk during which an implant is fixed in an intervertebral disk by means of a nail or pin.

The invention relates to a set for the endoscopic fixation of an implant in an intervertebral disk by means of a nail or pin. The set of instruments can be used in an operation at an intervertebral disk together with an endoscope which is conventionally used for such an operation. Here, the set according to the present invention comprises the following:

- an applicator sheath which can be introduced through an endoscope into an intervertebral disk and through which an implant can be inserted into an intervertebral disk defect;
- a drill wire guide sheath which is dimensioned such that it can be inserted into the applicator sheath; and
- a pusher for transmitting blows during the fixation of an implant in the intervertebral disk by means of a nail or pin, wherein the pusher is dimensioned such that it can be inserted into the applicator sheath.

A sheath is understood to be an elongated, hollow cylindrical body with a comparatively thin wall. This hollow cylindrical body can be largely rotationally symmetrical about a central longitudinal axis. However, this does not preclude certain areas of the sheath from deviating from this rotational symmetry and, for example, fulfilling special functionalities. This applies, in particular, to areas at the proximal or distal end of the respective sheath. The applicator sheath is preferably formed in one piece, but it can also be formed in several pieces. The drill wire guide sheath is also preferably made in one piece, but it can also be made in several pieces The applicator sheath can be introduced through an endoscope into an intervertebral disk. Preferably, the applicator sheath can be plugged on the endoscope and/or for the connection between the endoscope and the applicator sheath no further mounting part is required, in particularly no screw connection. Preferably, the applicator sheath also does not comprise a separate holder or handle so that it can be produced very easily.

The dimensions of the applicator sheath are preferably selected such that the applicator sheath at least in large parts can be introduced into the endoscope. Preferably, a part of the applicator sheath cannot be introduced into the endoscope, but it forms a stop unit for preventing that the whole applicator sheath unintentionally slides into the endoscope. This stop unit is not a holder or handle. In all embodiments, at the distal end of the applicator sheath, thus at the outermost end on the stop unit, a marker can be applied which shows the position of the beveled ground section of the sheath. In an alternative, in all embodiments, the marker can also be applied at the stop unit.

Similarly, the same applies to the drill wire guide sheath which is dimensioned such that it can be inserted, in whole or in part, into the applicator sheath. Also, here, it is preferred to provide a respective stop unit for preventing that the drill wire guide sheath completely slides into the applicator sheath. For allowing an insertion of the drill wire guide sheath into the applicator sheath, the inner diameter of the applicator sheath is adjusted to the outer diameter of the drill wire guide sheath. Preferably, here, a small clearance in the range of tenths of a millimeter is provided which facilitates the insertion, but due to the total length of applicator sheath and drill wire guide sheath in practice does not compromise the accuracy of the positioning of the drill wire guide sheath in the applicator sheath in the region of the proximal end of both sheaths. On the other hand, the inner diameter of the drill wire guide sheath has to be dimensioned such that a drilling wire can be guided through the drill wire guide sheath without any problems and, nevertheless, precisely.

The pusher of the set according to the present invention is suitable for transmitting blows during the fixation of an implant in the intervertebral disk by means of a nail or pin and it is intended for that. Preferably, therefore, the pusher is of compact design and it is not a hollow body. This increases the stability and facilitates the transmitting of blows or hammer blows during the fixation. Furthermore, the pusher is dimensioned such that it can be inserted into the applicator sheath. Here, the outer diameter of the pusher is accordingly adjusted to the inner diameter of the applicator sheath. Preferably, here, between the applicator sheath and the pusher a small clearance in the range of tenths of a millimeter is provided. This facilitates the insertion of the pusher into the applicator sheath, but does not compromise the precision of the positionability of the pusher. Here, preferably, the length of the pusher is selected such that the pusher is slightly longer than the applicator sheath, because, when blows are transmitted in connection with the fixation of an implant in the intervertebral disk by means of a nail or a pin, it is necessary that these blows can be carried out freely, namely without vibrations of the applicator sheath. Also, the pusher is preferably formed in one part from one workpiece, but it can also comprise several parts.

According to a preferred embodiment of the invention the applicator sheath comprises a beveled tip, a main body having a hollow cylinder design and a flange-like end piece. Here, the beveled tip is provided at the proximal end of the applicator sheath and the flange-like end piece is provided at the distal end of the applicator sheath. Thus, in functional view, here, the applicator sheath can be partitioned into three parts. The applicator sheath can be manufactured in one piece or several pieces. When the applicator sheath consists of several components, then they are preferably welded together or adhesively bonded. Here, the flange-like end piece is also of hollow design and, in particularly inside, it is seamlessly attached to the main body having a hollow cylinder design. In all embodiments, at the distal end of the applicator sheath, thus at the outermost end on the stop unit, a marker may be applied which shows the position of the beveled ground section of the sheath. In an alternative, in all embodiments, the marker may also be applied at the stop unit.

However, the outer diameter of the flange-like end piece is larger than the outer diameter of the main body having a hollow cylinder design, so that a sliding of the applicator sheath into the endoscope can be prevented. The beveled tip is preferably provided by one or more recesses at the proximal end of the applicator sheath or the hollow cylindrical main part. Thus, preferably, an outer diameter of the applicator sheath is not reduced in the region of the beveled tip. The maintaining of the outer diameter results in the fact that other constituents of the set of instruments as well as also further parts which have to be guided through the applicator sheath actually have place in it without any problems. Here, the beveled tip provides the advantage that endoscopically the view to the nail or pin, the implant and the optionally used drilling wire is free, and so it is possible to guarantee that the nail or pin really fastens the implant. According to an embodiment of the invention, the beveled tip comprises at least one, preferably two or several tip ends which are formed by recesses in the applicator sheath. In addition, or in an alternative, the tip of the applicator sheath relating to the longitudinal axis of the applicator sheath is beveled in a rotationally asymmetrical manner. The tip ends are used for an exact positioning of the applicator sheath during the operation in the intervertebral disk interspace by contact at the adjacent vertebral body.

Here, the tip ends are preferably blunt so that they will find grip, but do not result in injuries. The tip ends are used for the stabilization of the applicator at the point of contact. For example, the tip ends may have the form of blunt teeth. They may comprise a narrow, in particularly rounded area of contact or line of contact. The rotationally asymmetric beveling of the tip of the applicator sheath facilitates the interplay of the set of instruments with the used endoscope. The rotationally asymmetric beveling results in the fact that the tip ends are at least not symmetrical in a plane through which the longitudinal axis of the applicator sheath passes. In the simplest case, both recesses in the case of two tip ends of the beveled tip are each described geometrically by a section with one plane. When the main body having a hollow cylinder design of the applicator sheath is rotationally symmetrical, then this section results in respective ovals in the wall of the main body having a hollow cylinder design, whereby then the beveled tip is formed in the first place.

A preferred embodiment of the invention is characterized by the fact that the beveled tip is beveled in an rotationally asymmetrical manner with respect to the longitudinal axis of the applicator sheath and that it comprises two tip ends; and by the fact that both tip ends and at least one line passing therethrough which is parallel with respect to the longitudinal axis of the applicator sheath define at least one tip plane;

wherein relating to one tip plane an upper beveling of the tip is geometrically described by a section with an upper plane being inclined by an upper acute angle a with respect to this tip plane; and/or wherein relating to the same or a further tip plane a lower beveling of the tip is geometrically described by a section with a lower plane being inclined by a lower acute angle β with respect to this tip plane.

So, the production of a such formed applicator sheath can be conducted in a simple manner. In addition, in this way, the advantageous rotationally asymmetric design can be achieved which in turn results in respective advantages during the handling of the set according to the present invention.

Whether it is necessary to define one tip plane or two tip planes, mainly depends on the geometric form of both tip ends. When, for example, both tip ends are blunt having a certain height h, then it is possible to define one tip plane each at the upper end and at the lower end of both tip ends with the height h. In this case, there are two tip planes at which by a section with the applicator sheath in the angles α and β, respectively, a recess can be generated so that the tip correspondingly comprises an upper beveling and a lower beveling. However, when both tip ends are really pointed, then there is only one single tip plane and this plane then also directly passes through the tips of both tip ends. In this case, the two angles α and β also abut each other directly.

According to a preferred embodiment of the invention $20° \leq \alpha \leq 30°$ applies for the upper acute angle, preferably $\alpha = 25°$. Additionally, or alternatively, $20° \leq \beta \leq 30°$ applies for the lower acute angle, preferably $\beta = 25°$.

According to a further preferred embodiment of the invention, the two tip ends have a height h orthogonal to the longitudinal axis of the applicator sheath for which holds: 0.5 mm≤h≤1.5 mm, preferably h=1.0 mm. In this case, the two tip ends are therefore blunt, and can form a narrow, rounded contact area or a contact curve on contact with an intervertebral disk, in particular.

According to another preferred embodiment of the invention, the beveled tip comprises several, preferably three to five, tip ends which are formed by recesses in the applicator sheath.

According to a preferred embodiment variant of the invention, the drill wire guide sheath comprises a hollow cylindrical main part and a flange-like end piece. The flange-like end piece forms a stop when inserting the drill wire guide sheath into the applicator sheath. The flange-like end piece itself is also hollow and preferably it seamlessly joins the cavity inside the hollow cylindrical main part of the drill wire guide sheath. The drill wire guide sheath is preferably the same length or shorter than the applicator sheath including the tip ends.

According to an embodiment of the invention, the pusher comprises a mandrel at its proximal end, a cylindrical main part and a pusher header at its distal end. In this case, preferably, the mandrel, the cylindrical main part and also the pusher header are compact and thus essentially non-hollow. In this case, the outer diameter of the mandrel is significantly smaller than the outer diameter of the cylindrical main part, and the outer diameter of the cylindrical main part is in turn smaller than the outer diameter of the pusher header. The mandrel is considered to be the point of application for a nail or pin, which have a notch. The precise fit of the mandrel in the notch of a nail or pin enables optimal mediation of blows during fixation of an implant in the intervertebral disc by means of a nail or pin, since the force and/or pressure applied during the blow is optimally transmitted to the head of a nail or pin.

The pusher with its three functional constituents mandrel, cylindrical main part and pusher header can be manufactured in one or more parts. Preferably, the mandrel and the main part are manufactured in one part, and later the pusher header is fastened separately. Preferably, the individual components of the pusher are welded or glued together if they were manufactured separately.

According to another embodiment of the invention, the pusher is formed of a cylindrical main part and a pusher header at its distal end as already described, however, in this embodiment, the plusher does not have a mandrel at its proximal end. In connection with this embodiment, preferably, nails or pins are used which do not comprise a notch at its head end, and thus a pusher without a mandrel shows a better mediation of blows during the fixation of the implant.

Here, for the dimensions of the pusher and/or its parts, preferably, the following dimensions apply:

- a length LSK of the pusher header along the longitudinal axis of the pusher is: 13 mm≤LSK≤17 mm, preferably LSK=15 mm; and/or
- for an outer diameter DSK of the pusher header the following applies: 8 mm≤DSK≤12 mm, preferably DSK=10 mm; and/or
- for the length LD of the mandrel along the longitudinal axis of the pusher the following applies: 1.9 mm≤LD≤2.1 mm, preferably LD=2.0 mm; and/or
- for the outer diameter DD of the mandrel the following applies: 0.9 mm≤DD≤1.1 mm, preferably DD=1.0 mm.

The outer diameter DSK of the pusher header allows for the simplest and most accurate placement of blows or hammer blows. The dimensions of the cylindrical main part are adjusted to the applicator sheath and its inner diameter. The mandrel of the pusher is adapted in its dimensions to the dimensions of a usable nail or pin with notches on the head part or is preferably not present in an embodiment in which the nail or pin has no notch.

According to a further preferred embodiment variant, the outer diameters and inner diameters of the instruments of the set are adapted to each other as follows:

- for an outer diameter DA of the applicator sheath the following applies: 3.9 mm≤DA≤4.1 mm, preferably large DA=4.0 mm; and
- for an inner diameter dA of the applicator sheath the following applies: 3.3 mm≤dA≤3.5 mm, preferably dA=3.4 mm; and
- for an outer diameter DB of the drill wire guide sheath the following applies: 2.9 mm≤DB≤3.1 mm, preferably DB=3.0 mm; and
- for an inner diameter dB of the drill wire guide sheath the following applies: 2.3 mm≤dB≤2.5 mm, preferably dB=2.4 mm; and
- for an outer diameter DS of the pusher the following applies: 2.9 mm≤DS≤3.1 mm, preferably DS=3.0 mm.

For successful endoscopic fixation of an implant in an intervertebral disc using a nail or pin, the lengths of the applicator sheath, the drill wire guide sheath and the pusher are also preferably matched.

Preferably, the following relations apply:

- for a length LA of the applicator sheath the following applies: 250 mm≤LA≤290 mm, preferably LA=270 mm; and
- for a length LB of the drill wire guide sheath the following applies: 245 mm≤LB≤285 mm, preferably LB=265 mm; and for a length LS of the pusher the following applies: 265 mm≤LS≤305 mm, preferably LS=285 mm; and furthermore, according to this embodiment, the following applies: LB<LA<LS;

wherein the specified lengths LA, LB and LS are determined in the case of the presence of a flange-like end piece or a header at the respective component without the respective flange-like end piece or without the header.

According to another preferred embodiment, the following relations are valid:

for a length LA of the applicator sheath the following is valid: 215 mm≤LA≤290 mm, preferably LA=230 to 250 mm, particularly preferably 235 to 245, most preferably 240 mm; and for a length LB of the drill wire guide sheath the following is valid: 210 mm≤LB≤285 mm, preferably LB=230 to 240 mm, particularly preferably 235 mm; and for a length LS of the pusher the following is valid: 220 mm≤LS≤305 mm, preferably LS=250 mm to 260 mm, particularly preferably 255 mm; and furthermore, according to this embodiment, the following is valid: LB<LA<LS;

wherein the indicated lengths LA, LB and LS are determined in the case of the presence of a flange-like end piece or a header at the respective component without the respective flange-like end piece or without the header.

In a particularly preferred embodiment, the following relations apply:

for a length LA of the applicator sheath the following applies: 215 mm≤LA≤290 mm, preferably LA=230 to 250 mm, particularly preferably 235 to 245, most preferably 240 mm; and for a length LB of the drill wire guide sheath the following applies: 210 mm≤LB≤285 mm, preferably LB=230 to 240 mm, particularly preferably 235 mm; and for a length LS of the pusher the following applies: 220 mm≤LS≤305 mm, preferably LS=250 mm to 260 mm, particularly preferably 255 mm; and furthermore, according to this embodiment, the following applies: LB<LA<LS;

wherein the indicated lengths LA, LB and LS are determined in the case of the presence of a flange-like end piece or a header at the respective component without the respective flange-like end piece or without the header. Furthermore, in this embodiment, the pusher which is formed by a cylindrical main part and a pusher header at its distal end does not comprise a mandrel at its proximal end. Along with this embodiment, preferably, nails or pins are used that do not have a notch at their head end, and thus a pusher without a mandrel has better mediation of blows during fixation of the implant.

In all embodiments, the slight shortening of the drill wire guide sheath compared to the applicator sheath ensures that a drill wire inserted through the drill wire guide sheath has sufficient clearance when pre-drilling a hole within the disc or vertebral body. It also provides the least obstruction to the view through the endoscope. The pusher, in turn, is longer than the applicator sheath so that when the nail or pin is fixed within the intervertebral disc, the blows can be performed without obstruction or essentially without transfer to the applicator sheath. The pusher is approx. 2 mm to 50 mm, preferably 5 mm to 40 mm, most preferably 10 mm to 20 mm and most of all preferably approx. 15 mm longer than the applicator sheath.

According to a further preferred embodiment of the invention, for a length LFA of a flange-like end piece of the applicator sheath along the main axis of the applicator sheath and for an outer diameter DFA of the flange-like end piece of the applicator sheath the following relations apply: 2.9 mm≤LFA≤3.1 mm, preferably LFA=3 mm; as well as 9 mm≤DFA≤11 mm, in particularly DFA=10 mm.

In addition, or in an alternative, for a length LFB of a flange-like end piece of the drill wire guide sheath along the main axis of the drill wire guide sheath and for an outer diameter DFB of the flange-like end piece of the drill wire guide sheath the following relations apply: LFB=LFA+0.1 mm, preferably LFB=3 mm; as well as DFB≥DFA, preferably DFB=12 mm.

If the outer diameter DFB of the flange-like end piece of the drill wire guide sheath is slightly larger than the outer diameter DFA of the applicator sheath, then after the drill wire guide sheath has been inserted with the applicator sheath in the stop or completely up to the stop, the drill wire guide sheath can be removed more easily from the applicator sheath due to the slight elevation in the area of the flange-like end piece compared to the end piece of the applicator sheath.

According to a further preferred embodiment, the components of the set are reusable after suitable sterilization. Preferably, the applicator sheath, the drill wire guide sheath and the pusher each comprise at least one of the following listed materials: primarily stainless steel, in particularly surgical steel, such as for example the following steel compositions:

M. No. 1.4016 (X6Cr17), AISI 430;

M. No. 1.4021 (X20Cr13), AISI 420;

M. No. 1.4301 (X5CrNi18-10), AISI 304, (V2A), SUS304;

M. No. 1.4404 (X2CrNiMo17-12-2), AISI 316L, (V4A, A4L);

M. No. 1.4452 (X13CrMnMoN18-14-3), P2000;

in particularly 1.4021, 1.4104, 1.4301, 1.4303, 1.4305, 1.4306, 1.4307, 1.4310, 1.4401, 1.4404, 1.4435, 1.4456, 1.4541, 1.4571, 1.4028, 1.4031, 1.4034, 1.4035, 1.4037, 1.4197, 1.4057, 1.4104, 1.4112, 1.4122, 1.4123, 1.4125, 9.9440, 1.4108, 1.4542, 1.4568 and 1.4543.

Furthermore, titanium and titanium materials can be used, as well as sterilizable plastics with the appropriate hardness. In particular, by mixing a wide variety of components, modern high-performance polymers, such as PEEK (polyether ether ketone plastics) or ceramic injection molding components (PIM/CIM process) with corresponding properties of hardness and elasticity, can achieve a stability comparable to that of steel if the products are designed appropriately and are thus suitable for use. High-performance polymers also behave similarly to metals when treated with chemicals, heat and UV light. Provided plastics of this category and quality are equally suitable. Furthermore, the components of the set according to the invention can be manufactured by 3D printing. In this respect, all materials known and used in 3D printing with corresponding properties can also be used. Preferably, surgical steel is used.

According to a further embodiment variant of the invention, in addition, the set comprises the following: a drill wire, in particularly a Kirschner wire (K wire) for predrilling a hole through an implant into the osseous part of a vertebral body. Preferably, such a drilling wire or K wire consists of surgical steel. It comes in different thicknesses. Here, the front end usually has a tip with or without thread. The rear end may have a fastening device for attaching a drill.

Preferably, the drilling wire has a length of at least 35 mm. Advantageously, when using the drilling wire, approx. 10 mm to 40 mm, preferably approx. 35 mm, are used at the rear end for fastening in a drill. At the front end, the tip can thus protrude approx. 1 mm to 25 mm, preferably approx. 20 mm, from the application sheath.

According to a further embodiment of the invention, the set further comprises an implant for insertion into an intervertebral disc.

In the context of this invention, an implant is understood to be a natural or artificial material that can be implanted in the human or animal body and is intended to remain there permanently or at least for a longer period of time. Preferably, the implant consists of a resorbable material. Preferably, the term "implant" comprises a biological or artificial matrix, a biological or artificial tissue or tissue parts or combinations thereof; for example allogeneic, autologous, xenogeneic or artificial tissue; a natural extracellular matrix or acellular matrix or combinations thereof. Optionally, the implant may comprise cells or cell constituents. Preferably, a textile implant is used. This implant may, for example, be porous, spongy, compact, a felt, a fleece or mesh-like.

This implant is particularly well suited to maintaining disc height within a disc after a herniated disc. Another advantage is that cells can migrate and colonize to regenerate the defect. Typically, the implant is inserted into the disc defect through an endoscopic portal and/or the applicator sheath, for example, using grasping forceps. In this process, the implant is passed through the endoscopic portal and/or the applicator sheath in a state in which it occupies as little volume as possible or has a very small diameter.

According to a further preferred embodiment of the invention, the implant comprises at least one of the following materials: collagen; hyaluronan (hyaluronic acid); polyglycolic acid; polylactic acid and/or their respective copolymers; polycaprolactone; a natural membrane, in particularly periosteum, perichondrium and/or fasciae, as well as their modifications; alginate; agarose; fibrin; albumin containing material; polysaccharides and/or combinations thereof.

According to a further embodiment of the invention, the set further comprises at least one nail or pin for the fixation of an implant in an intervertebral disk. Preferably, the nail or pin consists of one or more resorbable material(s), in particular the resorbable nail or pin consists of one or more biologically degradable material(s), such as for example a polymer made of polylactic acid (PLA). Alternatively, the nail or pin may be radiopaque or resorbable and radiopaque. For example, a resorbable and radiopaque nail or pin may be made partially or entirely of hydroxyapatite.

The nails or pins present in the set, which are preferably absorbable and/or radiopaque, are geometrically dimensioned in such a way that they are particularly suitable for the intended use for fixation of an implant in an intervertebral disc. Preferably, the nail or pin has a diameter DN for which the following applies: 1.4 mm≤DN≤1.6 mm, preferably the diameter DN=1.5 mm. In addition, or alternatively, a nail or pin has a length LN for which the following relation applies: 10 mm≤LN≤30 mm. Most preferably, a resorbable nail or pin with the above-mentioned dimensions is used.

The foregoing embodiments of the invention may be combined in whole or in part, provided that no technical inconsistencies arise.

Figure 2:
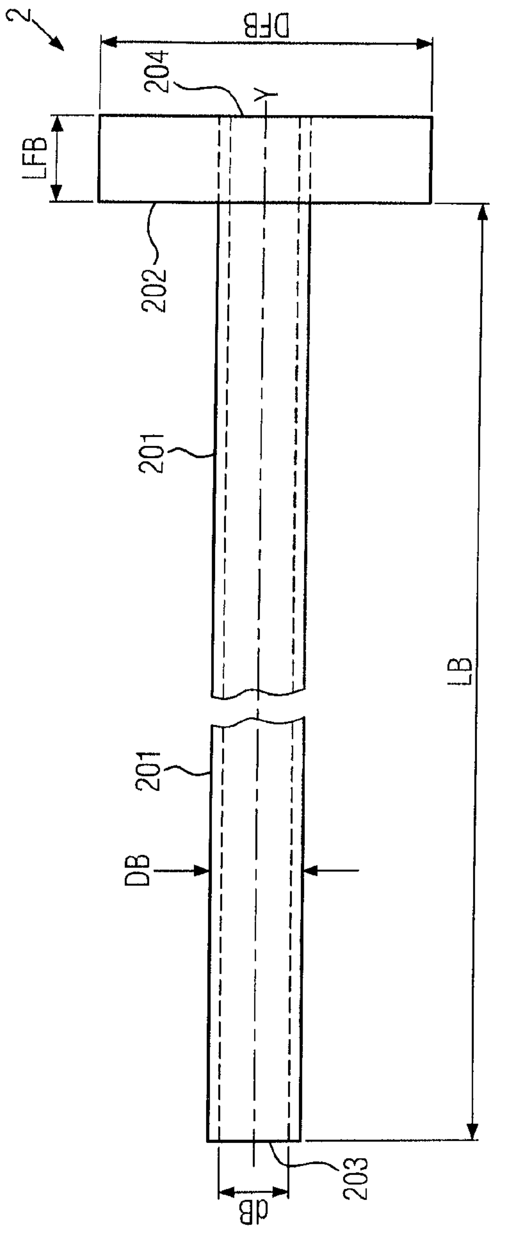
Figure 3:
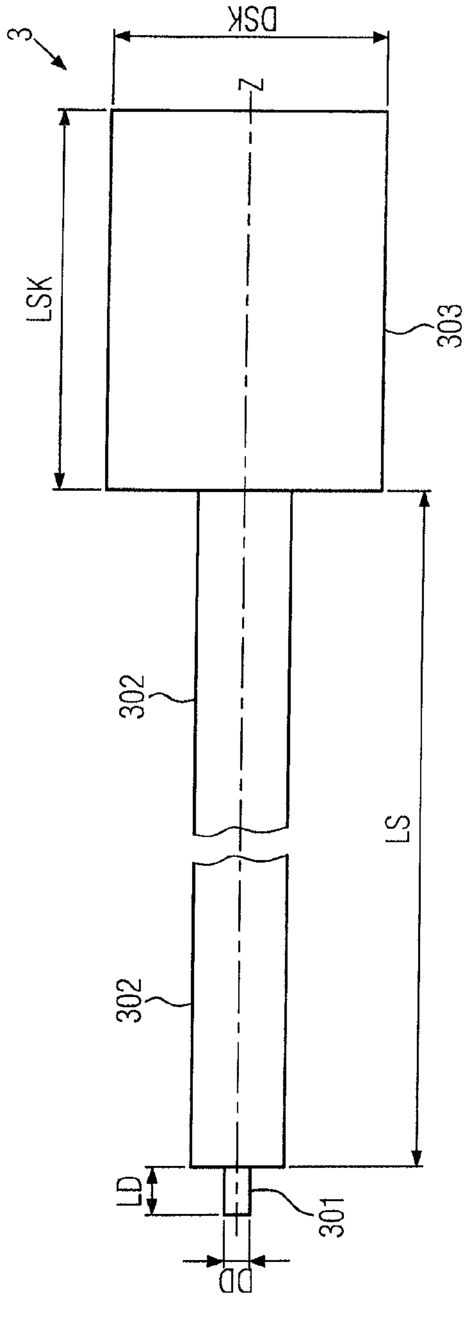

The invention will be understood even better with reference to the enclosed figures:

FIG. 1: shows an applicator sheath of a set according to the present invention;

FIG. 2: shows a drill wire guide sheath of a set according to the present invention;

FIG. 3: shows a pusher of a set according to the present invention;

FIG. 4: shows a table with typical dimensions of an applicator sheath, a drill wire guide sheath and a pusher for a set according to the present invention;

FIG. 5: shows exemplary dimensions including tolerances for a set according to the present invention with applicator sheath, drill wire guide sheath and pusher.

FIG. 1 shows exemplarily an applicator sheath 1 of a set according to the present invention for the endoscopic fixation of an implant in an intervertebral disk by means of a nail or pin. Thereby, FIG. 1*a*) shows a lateral sectional view of the applicator sheath 1 through the longitudinal axis X. FIG. 1*b*) shows a sectional view through the longitudinal axis X rotated by 90° to it in plan view. The applicator sheath 1 has a hollow cylindrical main portion 12, wherein a beveled tip 11 is disposed at the proximal end of the applicator sheath 1. At the distal end of the hollow cylindrical main portion 12 is a flange-like end piece 13. The beveled tip 11 is generated by recesses 18 and 19 in the cylindrical shell of the hollow cylindrical main portion 12.

The geometric relationships are shown in more detail in FIG. 1*a*). The beveled tip 11 has two tip ends 21 and 22. In FIG. 1*a*), these two tip ends lie congruently one behind the other, so that only the tip end 22 can be seen in the illustration in FIG. 1*a*). The two tip ends 21, 22 each have a tooth of height h, which is formed by the termination of the cylinder jacket of the applicator sheath 1. The beveled tip 11 is rotationally asymmetrically beveled with respect to the longitudinal axis X of the applicator sheath 1.

In the example shown in FIG. 1*a*), the two teeth 21, 22 therefore lie below the longitudinal axis X of the applicator sheath 1. The two tip ends 21, 22 and parallels to the longitudinal axis X of the applicator sheath 1 running through them define tip planes E1, E2. The planes E1 and E2 are mentally defined at the upper end of the tip ends 21, 22 and at the lower end of the tip ends 21, 22, respectively. With reference to the tip plane E1, an upper bevel 14 of the tip 11 is geometrically described by an intersection with an upper plane 14 inclined at an upper acute angle α with respect to this tip plane E1. Furthermore, with respect to the tip plane E2, a lower bevel 15 of the tip 11 is geometrically described by a section with a lower plane 15 inclined at a lower acute angle β with respect to the tip plane E2. The result of the performed cut is the recesses 18 and 19, which can be best seen in FIG. 1*b*).

FIG. 1 further shows the inner and outer diameters of the applicator sheath 1. The effective length LA of the applicator sheath 1 results in the direction of the longitudinal axis measured from the tip end to the beginning of the flange-like end piece 13. The flange-like end piece has a correspondingly larger outer diameter DFA as well as an additional length LFA. The inner diameter in the flange-like end piece 13 is the same as inside the hollow cylindrical main part 12.

FIG. 2 shows a drill wire guide sheath 2 of the set according to the present invention for the endoscopic fixation of an implant in an intervertebral disk by means of a nail or pin. The drill wire guide sheath 2 comprises a hollow cylindrical main part 201 as well as a flange-like end piece 202.

The drill wire guide sheath 2 has an inner diameter dB and an outer diameter DB. The effective length LB of the drill wire guide sheath 2 is preferably somewhat shorter than the effective length LA of the applicator sheath 1 in FIG. 1. The drill wire guide sheath 2 of FIG. 2 has an opening 203 at its proximal end. At its distal end, it has an opening 204 in the flange-like end piece 202 of the drill wire guide sheath 2.

Here, in the example shown, the outer diameter DFB of the drill wire guide sheath 2 is slightly larger than the outer diameter DFA of the flange-like end piece 13 of the applicator sheath 1. This enables easier separation of the drill wire guide sheath 2 and the applicator sheath 1 after the two stop units have been in contact with each other.

FIG. 3 shows a pusher for a set for the endoscopic fixation of an implant in an intervertebral disk. The pusher 3 shown is formed in one piece and comprises two or three different functional areas: An optional mandrel 301 at the proximal end, which may or may not be present depending on the embodiment, a cylindrical main part 302, as well as a pusher head portion 303 at the distal end. In the example shown, the pusher is formed to be completely compact, which allows for better transmission of force or pressure when imparting blows or hammer blows for fixation. The outer diameter DS of the pusher 3 and its cylindrical main part 302, respectively, is adjusted to the inner diameter dA of the applicator sheath 1.

Compared to this, the outer diameter DD of the mandrel is much smaller and also the length LD of the mandrel along the longitudinal direction or axial direction Z of the pusher 3 is extremely short and is only a few millimeters. The pusher head 303, on the other hand, is provided with a large outer diameter DSK and has a length LSK in the range of a few millimeters. Thus, the pusher head portion 303 is sufficiently large and solidly formed to be sufficiently stable when struck and to present a surface for the percussion instrument that is perpendicular to the longitudinal axis Z and large enough to be a target for blows.

The use of a set according to the invention for endoscopic fixation of an implant in an intervertebral disc by means of a nail or pin during an operation can be performed, for example, as follows: First, the applicator sheath 1 is inserted into the intervertebral disc through an endoscopic port. Subsequently, the implant is inserted through the applicator sheath 1 into the intervertebral disc defect, for example using grasping forceps. After removing the grasping forceps, the drill wire guide sheath 2 is inserted into the applicator sheath 1. By means of a drill wire, in particular a K-wire, a hole is drilled through the implant into the osseous part of the adjacent vertebral body. Subsequently, the drill wire is pulled out and the drill wire guide sheath 2 is also pulled out of the applicator sheath 1. At the same time, the angle to the drill hole should no longer be changed. In a next step a resorbable nail or pin is introduced into the applicator sheath 1 which slides through the sheath 1 up to the predrilled hole. By means of the inserted pusher 3, the nail can be driven into the pre-drilled hole in the vertebral body under short hammer blows. Thus, the head of the nail fixes the implant in the intervertebral disc.

The length ratios of applicator sheath 1, drill wire guide sheath and pusher 3 are matched to each other, and the same applies to their inner and outer diameters. The parts of the set shown in the FIGS. 1, 2 and 3 can be combined with each other in the manner shown.

FIG. 4 summarizes the length relationships and coordinated inner and outer diameters of applicator sheath 1, drill wire guide sheath 2 and pusher 3 in a corresponding overview once again. Here, the drill wire guide sheath 2 is slightly shorter than the applicator sheath 1 (LB slightly shorter than LA). On the other hand, the pusher 3 is correspondingly longer (LS>LA). The drill wire guide sheath 2 and the pusher 3 can be inserted one after the other into the applicator sheath 1. Accordingly, the outer diameters DB of the drill-wire guide sheath and DS of the pusher 3 in the example shown are the same at 3.0 mm. The wall thicknesses of applicator sheath 1 and drill wire guide sheath 2 are only a few tenths of a millimeter each. In contrast, the pusher 3 is of compact design.

FIG. 5 shows for a further exemplary embodiment variant dimensions and tolerances of applicator sheath 1, drill wire guide sheath 2 and pusher 3. The specified tolerances are permissible manufacturing tolerances which do not impair the functioning of the set according to the present invention. Here, the highest accuracy is required for the inner diameter dA of the applicator sheath 1 and the inner diameter dB of the drill wire guide sheath 2.

Here, manufacturing should be accurate to the tenth of a millimeter. The tolerance range for the outer diameter DB of the drill wire guide sheath 2 is slightly larger and is +0.04 mm. The same applies to the outer diameter DS of the pusher 3. Only then can it be ensured that the drill wire guide sheath 2 and/or the pusher 3 can be pushed through or inserted into the applicator sheath 1 without jamming or friction effects.

With the aid of the invention, it has been possible for the first time to provide a set for endoscopic fixation of an implant in an intervertebral disc by means of a nail or pin. It is hoped that this will result in significantly better long-term maintenance of the disc height during disc surgery.

What is claimed is:

1. A method for endoscopic fixation of an implant in an intervertebral disk comprising the steps of: (i) inserting an applicator sheath into an intervertebral disc defect through an endoscopic port; (ii) inserting an implant through the applicator sheath into the intervertebral disc defect; (iii) inserting a drill wire guide sheath into the applicator sheath; (iv) drilling a hole through the implant into an adjacent vertebral body; (v) removing the drill wire guide sheath from the applicator sheath; (vi) inserting an attachment device into the applicator sheath to the hole; (vii) driving the attachment device by a pusher into the hole in the vertebral body; and (viii) affixing the implant in the vertebra body by a securing device of the attachment device.

2. The method of claim 1, wherein an angle to the drill hole is not changed after step (iv).

3. The method of claim 1, wherein the attachment device is a resorbable nail or pin.

4. The method of claim 1, wherein the securing device of the attachment device is a nail head or pin head.

5. The method of claim 1, wherein driving the attachment device by the pusher is accomplished in a rhythm of short hammer blows.

* * * * *